(12) United States Patent
Putnam et al.

(10) Patent No.: US 6,794,191 B2
(45) Date of Patent: Sep. 21, 2004

(54) PROCESS FOR FORMING POLYMER STRUCTURES CONTAINING AN OXYGEN SENSOR

(75) Inventors: David L. Putnam, Sammamish, WA (US); Todd Hubbard, Lake Forest Park, WA (US)

(73) Assignee: Photonic Systems, Redmond, WA (US)

( * ) Notice: Subject to any disclaimer, the term of this patent is extended or adjusted under 35 U.S.C. 154(b) by 0 days.

(21) Appl. No.: 09/888,805

(22) Filed: Jun. 25, 2001

(65) Prior Publication Data

US 2003/0008400 A1 Jan. 9, 2003

(51) Int. Cl.[7] ............................................. G01N 21/00
(52) U.S. Cl. .............................. 436/1; 422/58; 422/61; 426/87; 426/232; 116/206
(58) Field of Search ............................. 436/1; 422/58, 422/61; 426/87, 232; 116/206

(56) References Cited

U.S. PATENT DOCUMENTS

| | | | |
|---|---|---|---|
| 3,067,015 A | * | 12/1962 | Lawdermilt et al. .......... 422/56 |
| 3,873,390 A | | 3/1975 | Cornell et al. |
| 4,657,736 A | | 4/1987 | Marsoner et al. |
| 4,810,655 A | | 3/1989 | Khalil et al. |
| 5,053,339 A | * | 10/1991 | Patel ............................ 436/2 |
| 5,185,038 A | | 2/1993 | Kamegawa |
| 5,407,829 A | | 4/1995 | Wolfbeis et al. |
| 5,869,341 A | * | 2/1999 | Woodaman .................... 436/1 |

FOREIGN PATENT DOCUMENTS

WO            98/15645    *    4/1998

* cited by examiner

*Primary Examiner*—Lyle A. Alexander
(74) *Attorney, Agent, or Firm*—Jeffrey B. Oster (57) ABSTRACT

There is disclosed a process for melting a luminescent oxygen sensitive compound into extruded polymer films. Specifically, there is disclosed a process for thermal melting of oxygen-sensitive indicators into common packaging polymers used for commercial packaging of products, such as foods. The oxygen-sensitive indicators can be used for real-time monitoring of oxygen in commercial packaging operations.

5 Claims, 8 Drawing Sheets

Figure 1b. Comparison of Stern-Volmer Response Characteristics for PtTPP and PdTPP in ethylene-octene copolymer
Comparison of PdTPP and PtTPP in LDPE Film

Figure 2a. Optical instrumentation used for lifetime measurements

Figure 2b. Ratio Response of PdTPP Dye in LDPE as a Function of Oxygen Concentration.

Figure 3. Emission spectra of PtOEP indicator in a thermal melt preparation of a commercial LDPE thermoplastic polymer. Excitation centered at 400nm.

Figure 4. Ratiometric Response Curves for Press-Plaques from Different Carrier Polymers Figure 5. Ratio response of a PtOEP film prepared by extrusion in twin-screw extrusion machine Figure 6. Various Laminate Forms of the Oxygen Sensor in Flexible Package Wrap Material

PROCESS FOR FORMING POLYMER STRUCTURES CONTAINING AN OXYGEN SENSOR

TECHNICAL FIELD OF THE INVENTION

This invention provides a process for fabricating oxygen-sensing polymers and methods for measuring the oxygen contents of packages and containers. In particular, this invention provides a process for the preparation and use of flexible polymer films containing an oxygen sensitive indicator and the instrumentation for quantifying said package's oxygen contents.

BACKGROUND OF THE INVENTION

There is a need for practical, economical, large-scale manufacturing and implementation of polymeric gas sensors with particular utility to the packaging industry. Packaging of oxygen sensitive foods, pharmaceuticals or medical supplies typically employs engineered gas barrier films and containers, inert gas flushes and high-speed heat-sealing equipment. There are no available technologies that provide a practical means for measuring in-package oxygen on a real time basis. In addition to packaging, many potential applications for oxygen sensing inside containers would benefit from the use of low-cost and sensor-containing barrier polymeric films.

Oxygen monitoring inside containers has required destructive lot testing and laborious, gas-sampling techniques. One common method requires that a needle be inserted into the headspace of a package and an air sample withdrawn for analysis. This method is prone to sampling errors, will result in loss of product (due to package integrity breech) and will provide only historical information rather than real-time data useful for process control. Therefore, there is a need for a non-invasive measurement method.

Optical sensors have been placed into a package and read via changes in absorbance, luminescent intensity or luminescent lifetime properties of the indicators. While these non-invasive optical sensors offer potential advantages over physical sampling techniques, they pose numerous practical disadvantages and added per-test costs to implement. Commonly described optical gas-sensor designs are prepared by casting or painting polymers dissolved in an organic solvent containing gas sensitive optical indicators (e.g., porphyrins, ruthenium, pyrenes) onto a substrate, such as glass, plastic or paper. The sensor can either be prepared as a distinct sensing coupon added to the package prior to sealing or it can be directly painted onto the inside surface of the package.

U.S. Pat. No. 4,810,655 (Khalil) describes an optical sensor cast from a volatile organic solvent solution of indicator and a carrier polymer cast onto a suitable inert substrate. Due to the nature of most suitable organic solvents, direct printing or painting onto flexible packaging using these sensor solutions has the potential for changing the engineered properties of these multilayer films including delamination, cracking, changes in film orientation and migration of processing additives. These problems provide significant hurdles to practical implementation of solvent-based casting, paint or printing methodologies. Other significant problems are inherent to solvent use, such as, flammability of the solvents, hazardous waste storage and removal, and the elimination of toxic fumes for worker safety.

Solventless approaches to preparing sensor films have been described (U.S. Pat. Nos. 4,657,736 and 5,407,829) by casting thin polymerizable films of ruthenium and a silicone copolymer onto food packaging films followed by completing the polymerization to form a sensor element. Although potentially minimizing effects on the packaging film and the other noted problems associated with solvent use, the equipment and logistics of applying and completing polymerization of the sensor material in the volumes necessary for the food packaging industry are well outside the common practice of film manufacturers. One further constraint to "painting" a sensor onto the overwrap material is the heat-sealing process used in most flexible packaging operations. Packaging films will have a sealing layer designed to provide a bond at specific parameters (e.g., temperature, dwell time) for the packaging machine. Application of even a thin polymer film in the sealing area can result in poor heat seals and package failure. Therefore, any process using "painted" sensors would require more elaborate film production equipment and orientation of the film during packaging than is commonly found in the industry.

In addition to the difficulty with preparing a practical optical sensor, it also has been difficult to implement an instrument for field use. Lifetime methods provide advantages of internal signal referencing that compensate for changes in signal path and oxygen-sensitive indicator concentration. Two such methods are based on phase-modulation or time-resolved determination of the luminescent lifetime. Although phase-modulation based methods can provide precise measures of lifetime, for applications with low concentrations of oxygen-sensitive indicator and irregular surfaces or sensor configurations with inconsistent reflection properties, the time resolved method provides greater immunity from correlated stray light (excitation) that can lead to non-reproducible performance of the phase-based method.

The addition of pigments to color polymer extrusions has been practiced (e.g., U.S. Pat. No. 5,185,038). Phosphorescent coatings have been prepared using a continuous hot-melt method (U.S. Pat. No. 3,873,390). Both methods use inorganic particles, luminescent or simply colored. In neither case is it suggested that these films would be useful optical gas sensing structures. Also common to patents for pigmenting polymers is the use of inorganic particles, luminescent or simply colored. As noted in Khalil (U.S. Pat. No. 4,801,655), a key element to creating useful luminescent oxygen probes from organic indicators such as porphyrins and chlorins is the complete dissolution of the indicator in the polymer. The thermal melt processes taught by this patent utilize a narrow window of gas-indicator thermal stability and polymer melt processing temperatures common to extrusion processes to form useful oxygen indicating structures.

SUMMARY OF THE INVENTION

The present invention provides a process for manufacture of oxygen sensitive polymeric structures by the addition of an oxygen-sensitive indicator directly to the thermal melt phase of polymers during extrusion processes. Preferably, the oxygen-sensitive indicator is luminescent. Importantly, the inventive process allows the integration of oxygen sensing functionality into polymer films, including multilayer barrier films common to the food packaging industry.

The present invention provides a process for making an oxygen-sensitive polymeric structure, comprising (a) adding an oxygen-sensitive indicator to a thermoplastic polymeric material heated to just above its melting temperature;

(b) mixing the oxygen-sensitive indicator thoroughly within the thermoplastic polymeric material while continuing the heating to maintain the thermoplastic polymeric material in a substantially liquid form; and (c) forming the mixture into an end product form of indicator-polymer product.

Preferably, the forming step is accomplished by an extrusion process, a molding process or an injection molding process. Preferably, the oxygen-sensitive indicator is selected from the group consisting of polycyclic aromatic hydrocarbons, pyrene, fluoranthene, decacyclene, diphenylanthracene, benzo(g,h,i)perylene), porphyrins, platinum or palladium octaethylporphyrin, tetraphenylporphyrin, tetrabenzporphyrin, chlorins, bacteriochlorins, isobacteriochlorins, chlorophyll), and combinations thereof. Preferably, the polymeric material is selected from the group consisting of linear ethylene alpha olefin copolymers, ethyl vinyl acetate, linear low-density polyethylene (LLDPE), very-low-density polyethylene (VLDPE), metallocene catalyzed polymers, and combinations thereof. Preferably, the melting temperature is from about 140° C. to about 240° C.

The present invention further provides a multi-layered food packaging film having an ability to detect oxygen presence within a packaging, comprising an indicator polymer product film and a plurality of non-oxygen sensing polymer films bonded thereto, wherein the indicator polymer product is made by a process comprising:

(a) adding an oxygen-sensitive indicator to a thermoplastic polymeric material heated to just above its melting temperature;

(b) mixing the oxygen-sensitive indicator thoroughly within the thermoplastic polymeric material while continuing the heating to maintain the thermoplastic polymeric material in a substantially liquid form; and (c) forming the mixture into an end product form of indicator-polymer product.

Preferably, the forming step is accomplished by an extrusion process, a molding process or an injection molding process. Preferably, the oxygen-sensitive indicator is selected from the group consisting of polycyclic aromatic hydrocarbons, pyrene, fluoranthene, decacyclene, diphenylanthracene, benzo(g,h,i)perylene), porphyrins, platinum or palladium octaethylporphyrin, tetraphenylporphyrin, tetrabenzporphyrin, chlorins, bacteriochlorins, isobacteriochlorins, chlorophyll), and combinations thereof. Preferably, the polymeric material is selected from the group consisting of linear ethylene alpha olefin copolymers, ethyl vinyl acetate, linear low-density polyethylene (LLDPE), very-low-density polyethylene (VLDPE), metallocene catalyzed polymers, and combinations thereof. Preferably, the melting temperature is from about 140° C. to about 240° C. Flexible polymeric materials commonly used to form oxygen barrier layers include poly (ethylene vinyl alcohol) (EVOH), polyacrylonitrile, polyvinyl chloride, poly(vinylidene dichloride), polyethylene terephthalate, polyamides, or combinations thereof. Preferably, the indicator polymer product is coextruded or laminated to one or more of these barrier-forming materials during manufacture of the film.

BRIEF DESCRIPTION OF THE DRAWINGS

FIG. 1a shows a laboratory instrument for determination of Stem-Volmer relationships. Specifically, the optical instrument consists of a (1) 50W Tg-Halogen source, (2) optical excitation filter(s), (3) collimation optics, (4) beam-splitter, (5) focusing optics, (6) target, (7) emission filters, (8) PMT and amplifier, and (9) a CPU for data collection and control.

FIG. 1b illustrates differences in responsivity engendered by two types of oxygen-sensitive indicators when used with the same polymer. Specifically, FIG. 1b shows the greater oxygen responsiveness of the PtTPP indicator-polymer signal in the range of 21% oxygen (room air) to approximately 1% oxygen when compared to the PdTPP indicator-polymer. In the lower oxygen ranges from 1% to less than 0.01%, the PdTPP indicator-polymer demonstrates a greater change in luminescent intensity (and lifetime) than the PtTPP indicator-polymer.

FIG. 2b shows an example of the luminescent ratio response as a function of oxygen concentration. PdTPP indicator was dissolved in an LDPE polymer film at 0.6 $\mu g/cm^2$ using thermal methods (as described in more detail in the examples below). The oxygen-sensitive film was placed in the gas-flush chamber and measured optically at oxygen levels ranging from 0% to 1.1% $O_2$/balance $N_2$.

FIG. 6 also shows "Laminate-b", the ratio response of the indicator-polymer laminated to an LLDPE film that in turn is laminated between two gas-barrier films.

DETAILED DESCRIPTION OF THE INVENTION

The present invention is an improved process for forming films having an oxygen-sensitive indicator dissolved directly into the thermally melted polymer phase common to plastic extrusion processes. The indicator-polymer product can then subsequently be shaped in a thermal melt form to fabricate oxygen-sensory structures of desired configuration via extrusion or molding processes (e.g., injection molding).

Alternatively, the indicator-polymer can be cut, skived or otherwise mechanically machined into a desired configuration by manufacturing processes practiced in the plastics industry. A preferred embodiment is to fabricate the indicator-polymer in a thin film form with the objective of promoting rapid transfer of gas through the material.

The inventive process provides particular utility and economy towards fabrication of films used for packaging including multi-layer laminates and coextruded films containing the indicator-polymer material in at least one layer of these films, for example, with extrudable polymers and copolymers useful in the packaging field including, for example, linear ethylene alpha olefin copolymers such as ethyl vinyl acetate, LLDPE, VLDPE, and metallocene catalyzed polymers. In addition to films, other polymer shapes can be made, such as, caps, cap liners, lids, bottles, and rigid containers that incorporate the oxygen-sensitive indicator. Preferably, the oxygen sensing indicator is luminescent. Most preferably, the oxygen-sensitive indicator is selected from the group consisting of polycyclic aromatic hydrocarbons (i.e., pyrene, fluoranthene, decacyclene, diphenylanthracene, and benzo(g,h,i)perylene), porphyrins (i.e., platinum or palladium octaethylporphyrin, tetraphenylporphyrin, tetrabenzporphyrin, chlorins, bacteriochlorins, isobacteriochlorins and chlorophyll), and combinations thereof. A common characteristic of these oxygen-sensitive indicators is solubility in the thermal-melt polymers such as those used in flexible film packaging. Furthermore, the oxygen-sensitive indicators are thermally stable at the temperatures required for thermoplastic fabrication. Complexes such as ruthenium(II)tris(bipyridyl) complexes, osmium (II)tris(bathophenanthroline) are not ideal candidates due to their poor solubility in the polymer melt.

Preferred oxygen-sensitive indicators include platinum (Pt) and palladium (Pd) chelate derivatives of octaethyl porphine (PtOEP & PdOEP respectively), and similarly Pt- & Pd-tetraphenyl porphine (PtTPP & PdTPP), and Pt- & Pd-tetrafluoro porphine (PtTFPP & PdTFPP). The PtTPP & PdTPP oxygen-sensitive indicators have advantages in cost. Additionally, they have low solubility in typical extraction test conditions important for compliance with FDA and USDA safety guidelines regarding extractables. The TFPP oxygen-sensitive indicators have oxidation stability (primarily photooxidation) and are useful for long-term storage and monitoring of oxygen

| Luminescent Indicator | Lifetime millisec | % Quantum Yield | Optimal Oxygen Range | Other |
|---|---|---|---|---|
| PtOEP | 0.13 | 90% | 21%–1% | |
| PdOEP | 1.96 | 50% | 2%–0.005% | |
| PtTPP | 0.25 | 45% | 21%–1% | more stable to oxidation than OEP - low cost |
| PdTPP | 2.0 | 20% | 2%–0.005% | |
| PtTFPP | 0.12 | 50% | 21%–1% | greater stability than TPP |

The optimal ranges of oxygen measurements depend upon the associated metal ligand. Platinum ligands, with natural decay lifetimes of 70–100 $\mu s$, are useful for determining oxygen concentrations in the range of 21% to 1%. Palladium ligand indicators, such as PdTPP, have natural decay lifetimes greater than 1 ms and are useful for determination of oxygen concentrations below 2%. Hafnium chelates can provide even lower oxygen sensitivities.

The thermal melt of the indicator-polymer can be further processed in any of a number of ways, including mixing and dilution with more of the same base polymer; mixing with other polymers; coextrusion with the same or other polymers; extrusions as a film; incorporation as a film with other layers of films to form multilayered products. In the case of multilayered products, the different layers are designed to provide particular functionalities, such as, adhesive layers to provide bonding properties. In a preferred embodiment for packaging applications to determine the oxygen within a sealed environment, a thin film indicator polymer layer made by the inventive process is incorporated into a package or vessel lidding material having an outer oxygen barrier layer, and additionally juxtaposed on the side internal to the package, an oxygen-permeable food safe contact layer.

In one embodiment, the oxygen-sensing characteristic of the polymer product, or the oxygen in an environment, is visually ascertained by placing a thin piece of indicator-polymer film into an environment wherein the oxygen content is to be sensed. The color characteristic or luminscent properties of the oxygen-sensitive indicator changes in an oxygen dependent manner. By irradiating the polymer product with light (electromagnetic radiation) of appropriate spectral characteristics one can visually ascertain the response of the polymer product to the oxygen present.

Alternatively, one can measure the oxygen in the environment in which the indicator product is placed using optical instrumentation. In this scenario, electromagentic radiation is directed at the polymer product. A signal of electromagnetic radiation returned by the polymer product containing an oxygen-sensitive indicator is captured by an optical detector. The intensity of the return signal and its luminescent lifetime change in an oxygen concentration dependent manner.

Instrumentation for Intensity-Based Luminescent Signal Measurements of Oxygen

Figure 1:
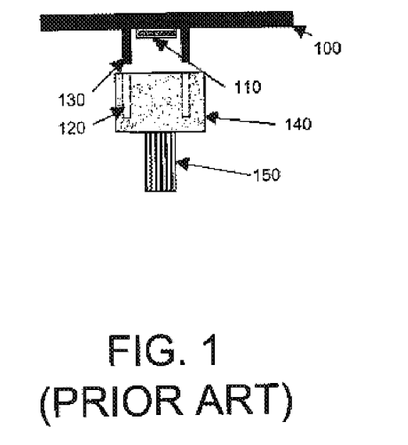

A laboratory instrument for determination of Stern-Volmer relationships is shown in FIG. 1a. The optical instrument consists of a (1) 50W Tg-Halogen source, (2) optical excitation filter(s), (3) collimation optics, (4) beamsplitter, (5) focusing optics, (6) target, (7) emission filters, (8) PMT and amplifier, and (9) a CPU for data collection and control. The sample of indicator-polymer is held in a gastight chamber connected to a vacuum pump. An electronic pressure gauge measures the chamber pressure. The computer initiates a measurement cycle at atmospheric pressure (21% oxygen) and records the luminescent intensity as a function of the gauge pressure. The vacuum system modulates the pressure and thereby the oxygen content that the sample is exposed to within the chamber vessel.

Figure 1B:
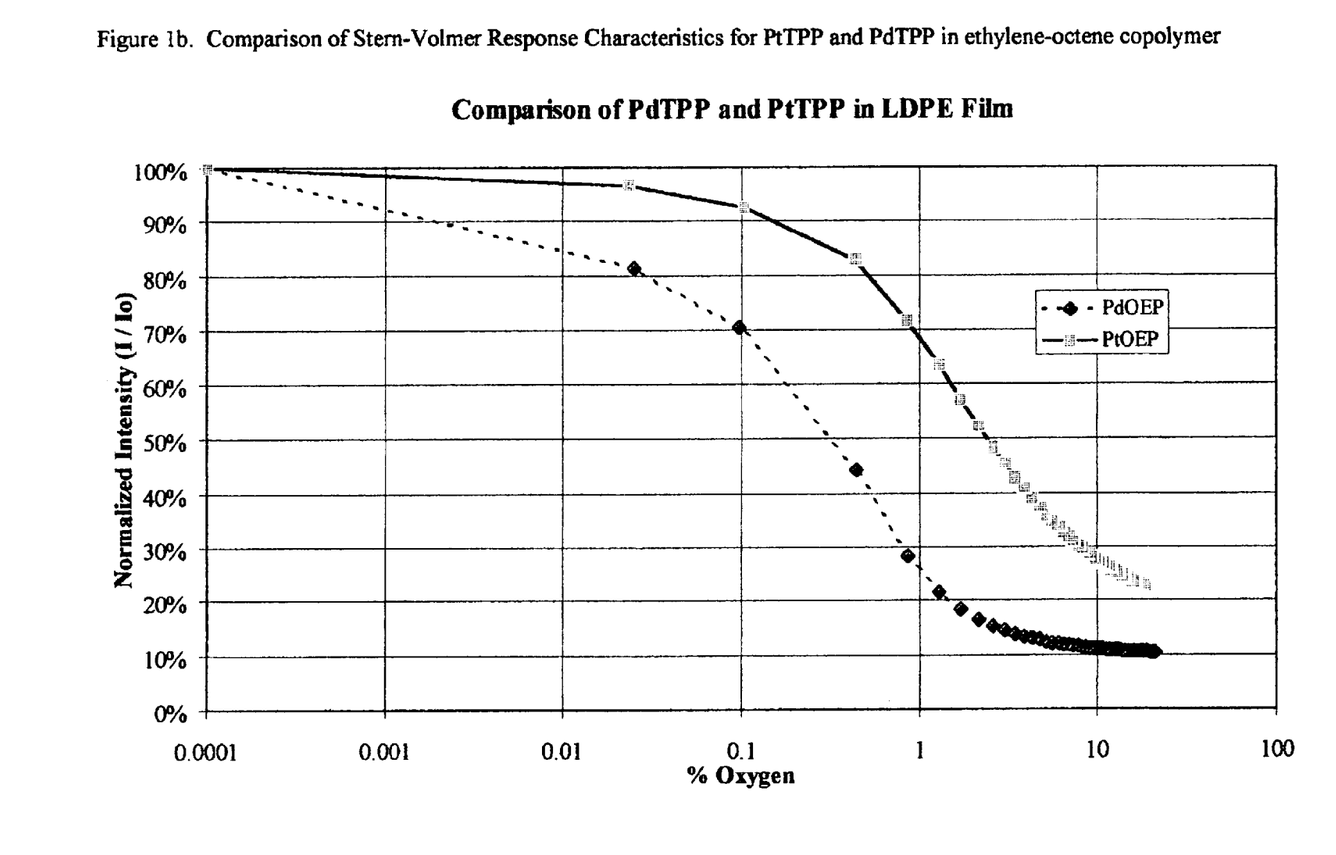
FIG. 1b shows examples of Stem-Volmer responses for PtTPP and PdTPP oxygen sensitive indicators dissolved in a LLDPE film prepared as described in the examples section).

The resulting data are plotted in a Stern-Volmer relationship ($I/Io$ vs $ln(P)$) where Io is the intensity measured with no oxygen quenching) to determine the characteristic response of the indicator-polymer to decreasing oxygen concentration. Examples of Stern-Volmer responses for PtTPP and PdTPP oxygen sensitive indicators dissolved in a LLDPE film (prepared as described in the examples section) are shown in FIG. 1b. FIG. 1b illustrates differences in responsivity engendered by two types of oxygen-sensitive indicators when used with the same polymer. Specifically, FIG. 1b shows the greater oxygen responsiveness of the PtTPP indicator-polymer signal in the range of 21% oxygen (room air) to approximately 1% oxygen when compared to the PdTPP indicator-polymer. In the lower oxygen ranges from 1% to less than 0.01%, the PdTPP indicator-polymer demonstrates a greater change in luminescent intensity (and lifetime) than the PtTPP indicator-polymer.

For oxygen levels above 5%, the low luminescent intensity of the Pd-indicators requires high gain PMT photodetectors, precision optics and attention to minimizing stray light to reliably measure the small luminescent signal. For example, measuring Pt-indicators at moderate oxgyen levels of 10% requires a PMT voltage of 400V compared to the Pd-indicator minimum of 900V (a gain difference of over $10^3$). The ability to select the most appropriate indicator based on the application's anticipated oxygen concentration is critical to the design of instrumentation optimally suited both financially and design wise for the industrial setting. This example also serves to illustrate the use of indicator-polymer to ascertain the pressure, or change of pressure in an environment, based on the measurement it yields of the oxygen content.

Instrumentation for Luminescent Lifetimes

Figure 2:
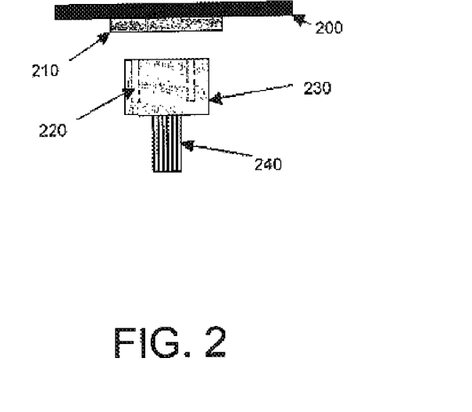
Figure 2A:
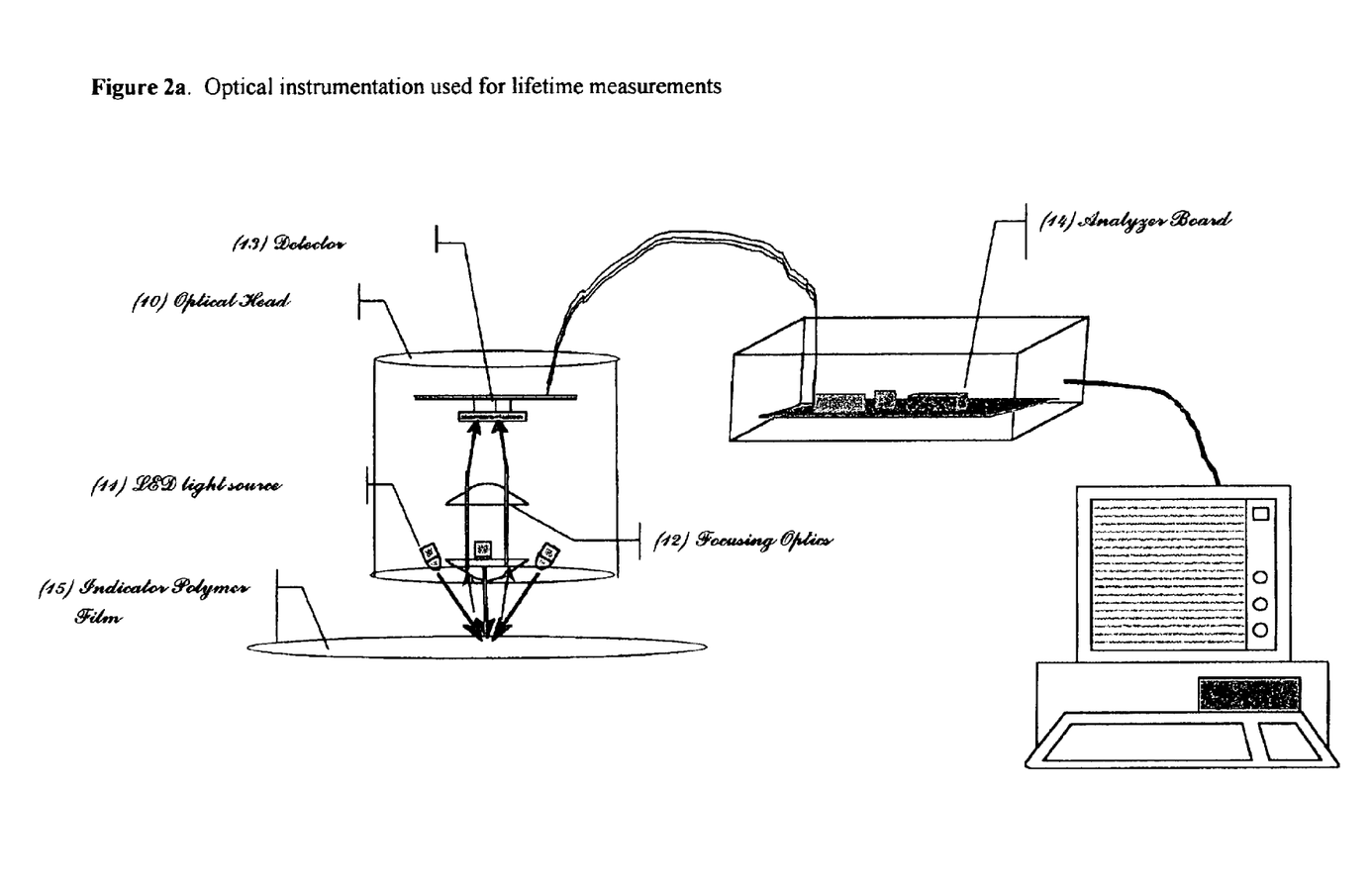
FIG. 2a shows the instrumentation components of the optical system used for making ratiometric luminescence lifetime measurements of oxygen sensitive indictor-ploymer films.

The instrument shown in FIG. 2a provides for ratiometric measurement of luminescent lifetime in a time domain. As a general instrument format, a light source modulated as a step function at a fixed frequency between 200 and 1500 Hz is focused onto the indicator-polymer test film sample (15) to excite the luminescent indicator molecules. The luminescent light from the indicator is collected by condensing optics and focused onto a photodetector. The signal is analyzed to determine its characteristic lifetime.

In a preferred format, an optical head (10) contains solid state light sources (11) (Nichia NLPB 500 LED—center wavelength at 450 nm) and focusing optics (12) and a detector (13) (Burr-Brown OPT210 high-speed integrated PIN-amplifier) are used. These parts are integrated in a hand-held optical head that is connected to the Ratiometric Lifetime Analyzer board (14). After compensating for low frequency ambient light, the Ratiometric Lifetime Analyzer estimates the luminescent signal's lifetime by integrating the electronic signal from two consecutive time periods during the signal decay ($I_1$ & $I_2$) and calculating the ratio of these two return intensities ($I_2/I_1$). The signal ratio is determined by a 12 bit A/D and output as a number from 1 to 4095. In this scheme, as the lifetime increases, the ratio of the two intensities increases. For the luminescent indicators quenched by oxygen, as the oxygen concentration goes down, $O_2$ quenching decreases, the luminescent lifetime increases and the ratio of $I_2/I_1$ increases as well. By adjusting the periods of $I_1$ and $I_2$, the instrument can be optimized for indicators with widely differing luminescent lifetimes and for any unique characteristics of the indicator-polymer.

In the preferred mode of use, the oxygen-sensitive indicator is present in the polymer product at concentrations imperceptible to the unaided eye (typically 0.155 ug/cm$^2$). Long integration times for the two consecutive time periods provides reproducible measurements for luminescent quenching in films containing very low concentrations of oxygen-sensitive indicator.

Figure 2B:
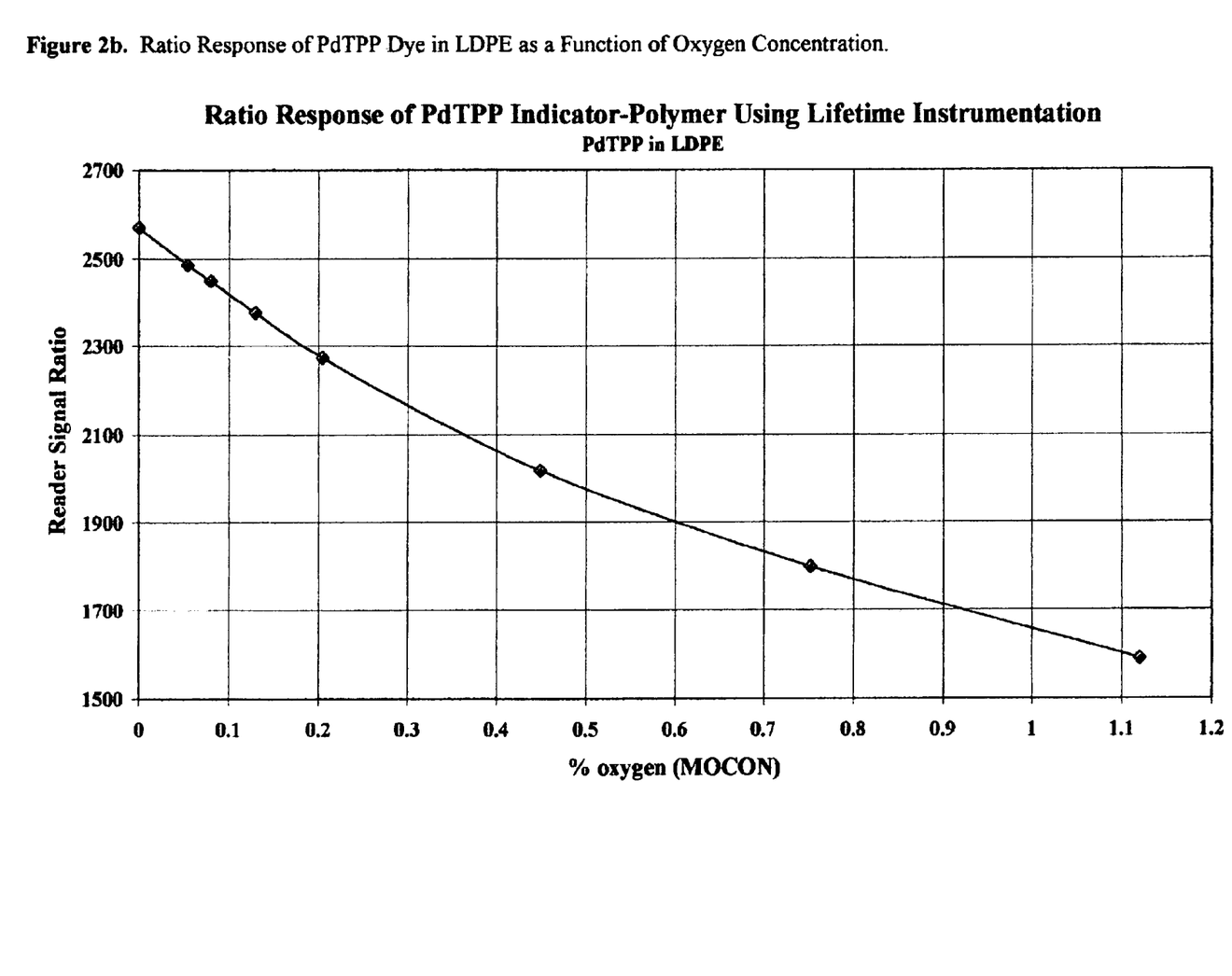

In general, a luminescent indicator-polymer's oxygen response was measured by placing a sample of it, preferably in the form of a film, in the window of a gas-flushed chamber. A Mocon oxygen analyzer, placed in line with the flush gas, provided a measure of the oxygen content in the chamber. The flush gas was modulated to yield different concentrations of oxygen such that the luminescent ratio responsive of the indicator-polymer sample can be measured at multiple known oxygen concentrations. An example of the luminescent ratio response as a function of oxygen concentration is shown in FIG. 2b. PdTPP indicator was dissolved in an LDPE polymer film at 0.6 $\mu$g/cm$^2$ using thermal methods (as described in more detail in the examples below). The oxygen-sensitive film was placed in the gas-flush chamber and measured optically at oxygen levels ranging from 0% to 1.1% $O_2$/balance $N_2$. The signal ratio as a function of the percentage of oxygen concentration is shown in FIG. 2b.

EXAMPLE 1

This example provides a process for producing a polymer-indicator product with commercial utility as a colorant masterbatch. Color concentrates are high-content mixtures of dye in a carrier resin most commonly used for coloration of a polymer film, sheet or molded part. Color concentrates or masterbatches, are mixed with process polymers to prepare colored parts. In this example, we describe methods for preparation of 3-different colorant masterbatches.

Figure 3:
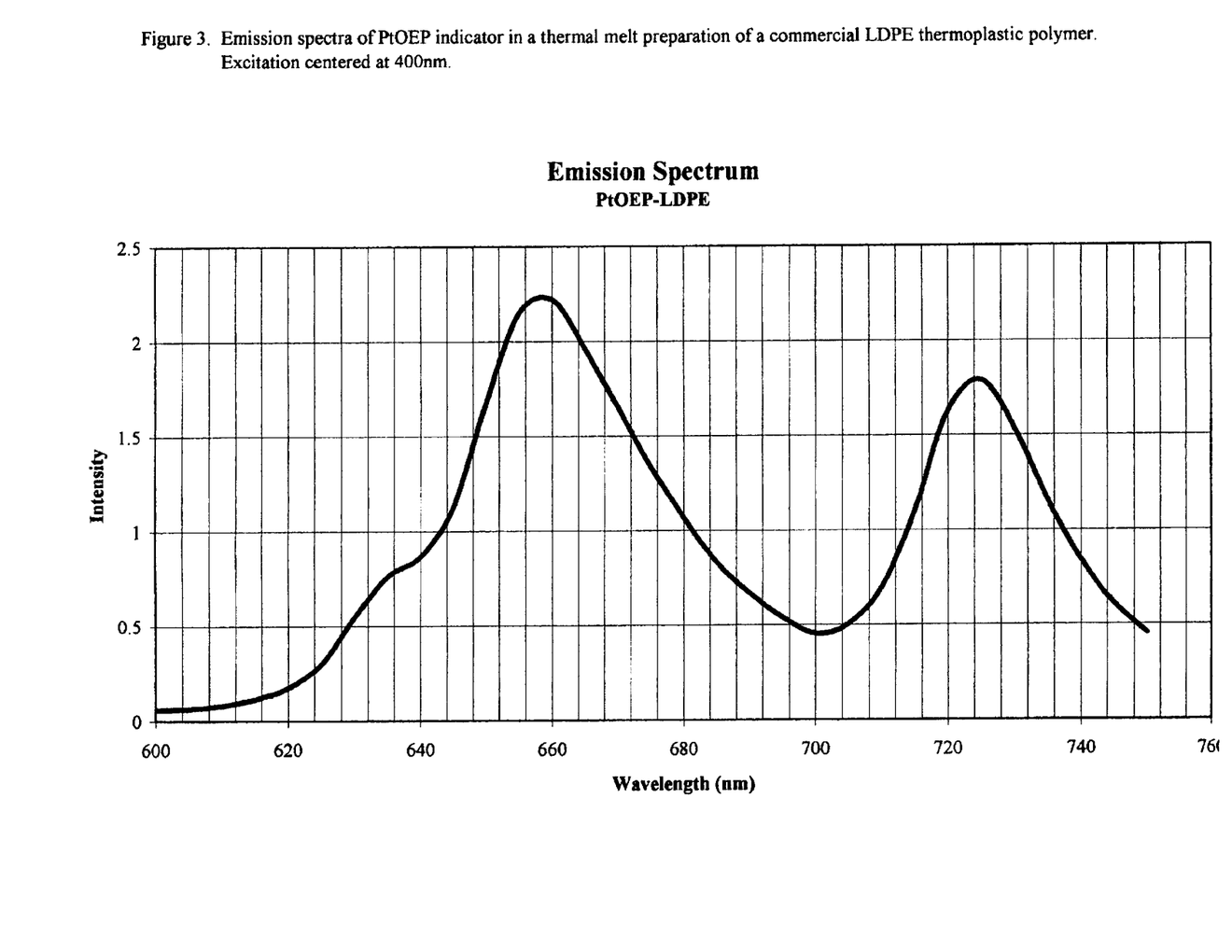
FIG. 3 shows a representative emission spectra (excitation at 400 nm) for a master batch of indicator polymer. The spectra of films are identical in their excitation and emission peaks to the dye in solution, indicating no thermal damage to the oxygen sensitive indicator during the polymer-indicator preparation.

100 Grams of a polyethylene-octene copolymer (Elite 5100, Dow Chemical) was added to the mix chamber of a Braebender mixer and melted at a temperature of 200° C. for approximately 5 minutes. One-gram of oxygen sensitive indicator (PtOEP) (Strem) was added to the polymer melt and mixed for an additional 7 minutes. The chamber was cooled to room temperature and the hardened polymer product was removed. Visual examination of the batch showed a homogeneously mixed material with no inclusions or exclusions of oxygen sensitive indicator noted. Fluorescence excitation and emission spectra of the material were measured using a SPEX Skin-Scan Fiber Optic Fluorometer at excitation wavelengths from 380 nm to 540 nm and emission wavelengths from 550 nm to 750 nm. A representative emission spectra (excitation at 400 nm) is shown in FIG. 3. The spectra of films are identical in their excitation and emission peaks to the dye in solution, indicating no thermal damage to the oxygen sensitive indicator during the polymer-indicator preparation. The product material (designated as PtOEP-Masterbatch #1) was chopped and used for production of test films as described in later examples.

In addition, a small-sample masterbatch was prepared by melting 5 grams of a linear low density polyethylene (Dowlex 2245, Dow Plastics) at 230° C. in a glass vessel and mixing 17 mg of PdTPP [Strem] into the polymer melt by hand until solubilization and blending was complete according to a visual examination. Again, no discoloration or indication of thermal damage was noted and fluorescence spectra showed no unexpected peaks. The product material (designated as PdTPP-Masterbatch #2) was chopped and used for production of test films as described in later examples.

A third masterbatch of indicator-polymer was prepared using a Rand-Castle Tabletop twin screw mixer-extruder by mixing 3-grams of oxygen sensitive indicator (PdTPP) to a process stream of a linear low-density polyethylene (Dowlex 2245, Dow Chemical). The final mix ratio of indicator to polymer was approximately 3:4,200 (w/w). Extruded indicator-polymer showed no visual or fluorescence excitation/emission spectra evidence of thermal degradation. This final example demonstrates methods that might be commercially useful for preparation of colorant masterbatches. It should be recognized by those practiced in the art that other thermal melt methods and machinery for preparing colorant masterbatches are to be included.

EXAMPLE 2

This example illustrates compounding polymer masterbatch products into carrier polymers including LLDPE's normally used in the manufacture of food packaging films. LLDPE refers to linear low-density polyethylene and copolymers of ethylene with one or more comonomers selected from preferably C4 to C10 alpha olefins such as octene. Commercially available examples of these include: Elite 5100—an ethylene-octene copolymer (Dow Plastics); Dowlex 2245—a low-density polyethylene (Dow Plastics). Rexene Pe1375 is an ethylene-vinyl acetate copolymer (Huntsman).

A 100-mg sample of PdTPP Masterbatch #2 was diluted by blending into 3 grams of undyed carrier polymer (ethylene-octene copolymer, Elite 5100). Pellets of the two materials were melted in a vessel heated to 200° C. and mixed thoroughly by hand for 4 minutes. The mixture was cooled to room temperature and the indicator-polymer was removed and cut into small pieces, each piece weighing approximately 100 mg each. A sample of the indicator-polymer mixture was subsequently reheated to 200° C. and pressed between two glass plates to form a thin film "press-plaque" approximately 1–2 mil thick. The final indicator concentration in the press plaque was approximately 0.6 $\mu g/cm^2$.

Press-plaques were also made using the PdTPP Masterbatch #2 mixed into the commercial polymers, Rexene and Dowlex 2245. Identical procedures as described above were used, substituting the Rexene or Dowlex polymers for the carrier polymer. In each of these cases, the final indicator concentration is estimated at 0.6 $\mu g/cm^2$ in the press-plaques.

Figure 4:
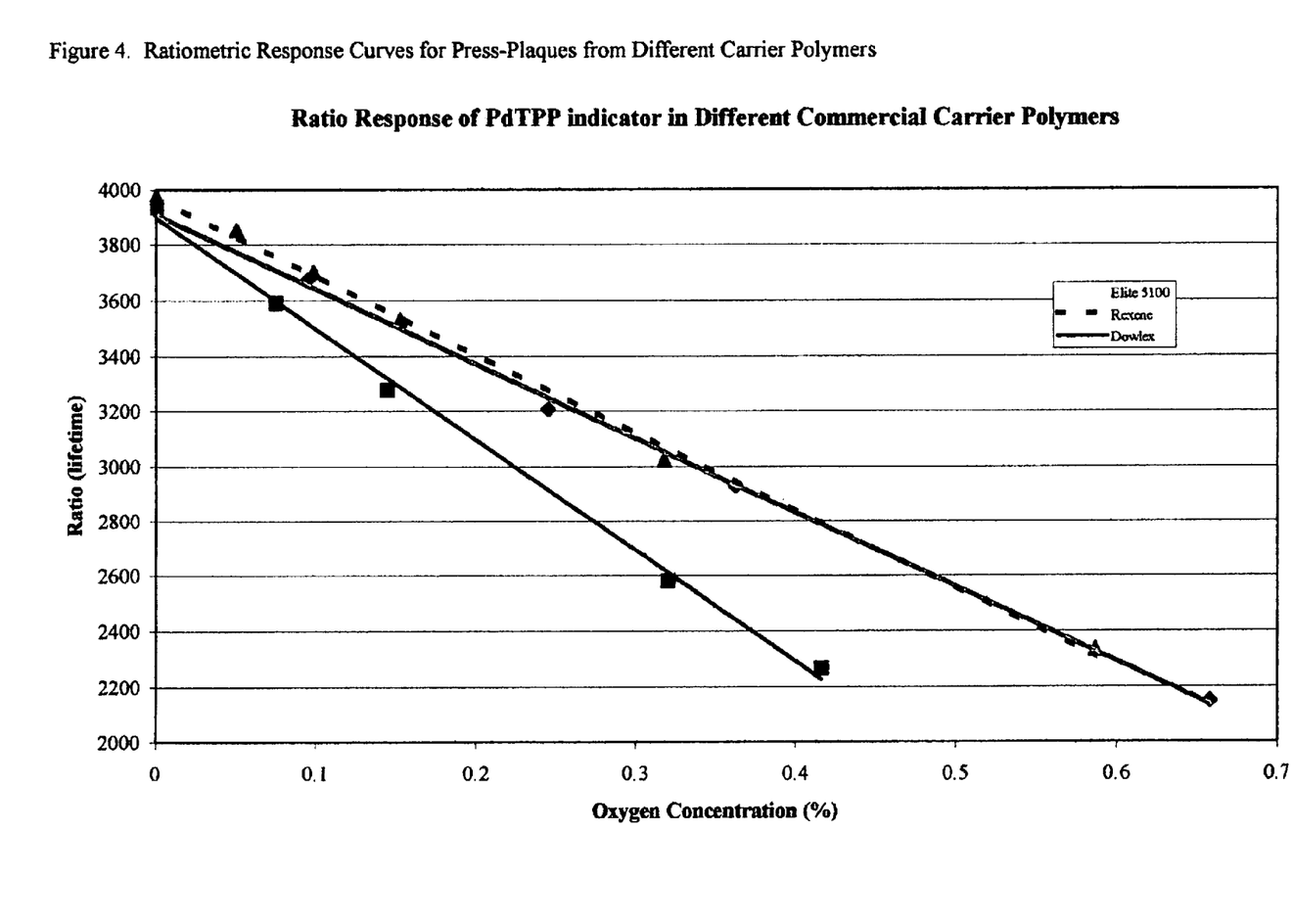
FIG. 4 shows the oxygen response results of three press-plaque sample films analyzed using the ratiometric lifetime instrumentation (of FIG. 2a) and gas-flush test system as described herein. The ratio response curves over the oxygen concentration ranges of 0% to 0.7% oxygen (0–700 ppm) for these three press-plaques are shown.

The three press-plaque sample films were analyzed using the ratiometric lifetime instrumentation and gas-flush test system described herein. The Ratio response curves over the oxygen concentration ranges of 0% to 0.7% oxygen (0–700 ppm) for these three press-plaques are shown in FIG. 4. These results in this figure demonstrate that the Ratio characteristics of the different polymer-indicator combinations differ slightly, as might be expected from the oxygen solubility differences between the three carrier polymers. However, any of these would be a suitable candidate for use in an oxygen-sensing layer of a laminate or multilayer film.

EXAMPLE 3

This example demonstrates the production of an extruded polymer film containing the indicator in a single layer of the extruded film. 100 grams of the PtOEP Masterbatch #1 (indicator-polymer) pellets prepared in Example 1 were added to the second hopper of a Rand-Castle Tabletop extruder. The process chamber temperature was maintained at 205° C. The polymer materials were calculated to have a 3–5 minute mean residence time in the extruder. The masterbatch material was mixed into a process stream of the commercial polymer, Elite-5100, in the extruder from which a film was extruded (¾ ft×100 ft×2 mil). The final indicator concentration of in the film was approximately 0.3 $\mu g/cm^2$. No signs of inclusions or gels or other anomalies were found thus indicating that the presence of the indicator did not create interferences with the extrusion process.

Figure 5:
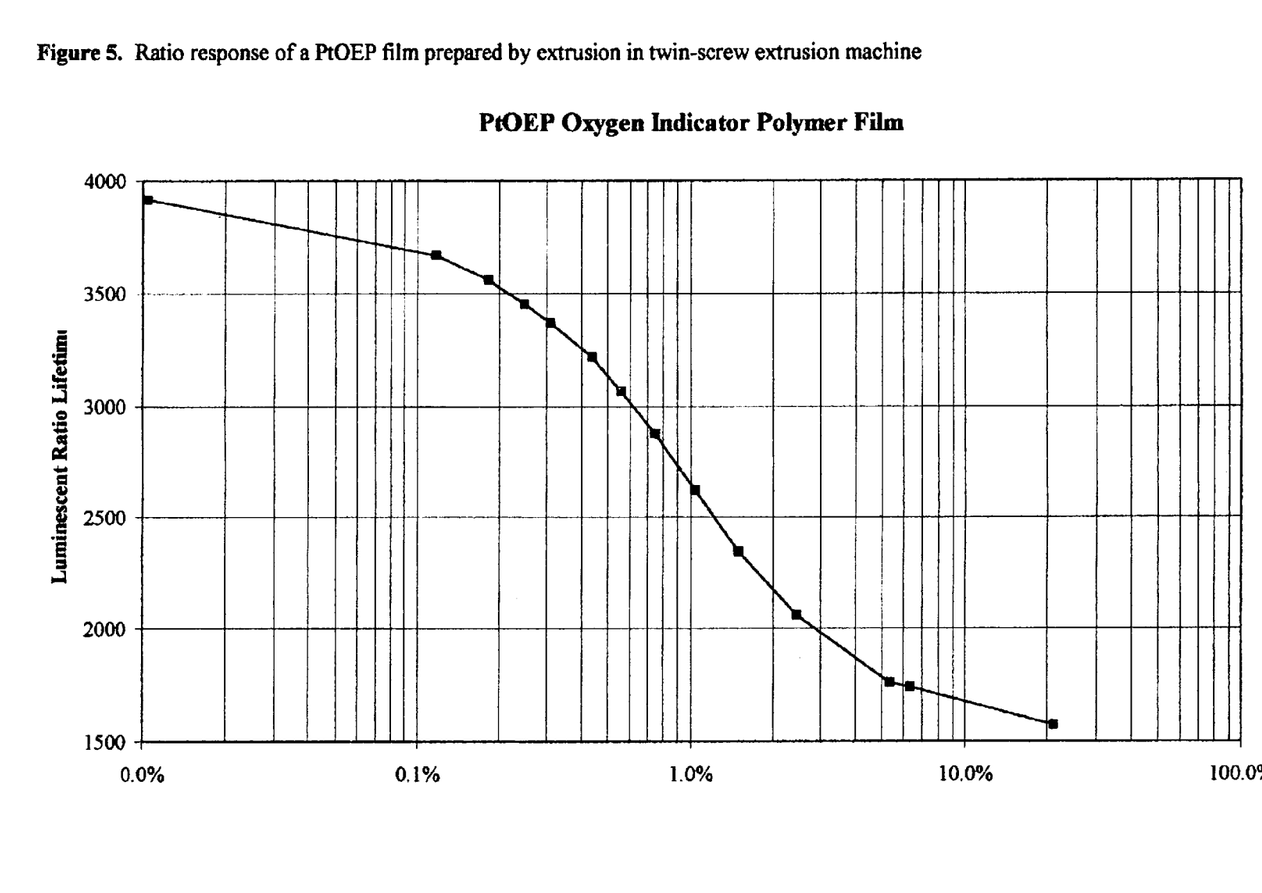
FIG. 5 shows the PtTPP indicator-polymer's luminescent lifetime as a function of oxygen concentration. Lifetime measurements of the film were made inside a gas flushed test vessel using the a "ratiometric" lifetime instrument over oxygen concentrations ranging from 21% to 0%. The maximal ratio change is in the 0.5% to 5% oxygen concentration range. This is contrasted with the Pd-based indicators described in Example 2 that have a maximal ratio change in the 0% to 1% oxygen concentration range.

The film had a slightly pink hue that visibly became brighter when placed in a low oxygen environment and illuminated with a "black-light". Coloration from the indicator was uniform throughout the 100-foot web of film. Luminescence intensity measurements were made at 10 separate areas along the film length, including the first and last foot of film, using the instrumentation described herein (FIG. 1a). Each of these measures demonstrated uniform oxygen responsivity along the web. Similarly, fluorescence spectra of the film were similar to each other and similar to spectra of the dye itself. Lifetime measurements of the film were made using the ratiometric lifetime instrumentation and gas-flush oxygen test vessel described herein and in FIG. 2b. The ratio response as a function of oxygen concentration (from 21% to 0%) is shown in FIG. 5. In this figure, note that the maximal ratio change is in the 0.5% to 5% oxygen concentration range. This is contrasted with a the Pd-based indicators described in Example 2 that have a maximal ratio change in the 0% to 1% oxygen concentration range.

These results show that indicator-polymer films prepared by extrusion are consistent along their length with respect to oxygen sensing and that the thermal processing parameters found in this extruder does not cause degradation of the indicator's oxygen sensing performance. Further, this example shows the utility of a PtOEP indicator polymer for measuring oxygen concentrations over the range of 21% to 1% oxygen.

EXAMPLE 4

This example describes visual sensing of oxygen responses. Indicator polymers produced in Example 1 were extruded into press plaque films made as described in Example 2. Sample pieces were placed into an environment where exposure to oxygen was modulated in the gas-flush test chamber described herein (Instrumentation for Luminescent Lifetimes). Directing light from a Blacklight (GE, F15T8-BLB) at the thin film samples containing approximately 0.3 $\mu g/cm^2$ of the Pt-porphyrin indicators (PtTPP or PtOEP), the indicator-polymers were visually seen to luminesce when exposed to ambient air (21% oxygen). The luminescent intensity increased visibly as the indicator polymers were exposed to decreasing concentrations of $O_2$ (21% to 1%) in the flush gas. The luminescence was clearly discernible at all oxygen concentrations and the displacement of oxygen could be visualized by the perceptible increase in the indicator-polymer film's intensity over the entire oxygen concentration range.

On the other hand, film samples prepared with the PdTPP indicator (PdTPP Masterbatches #2 and #3) similarly viewed under Blacklight illumination were thoroughly quenched by exposure to low oxygen concentrations of even a few percent such that no luminescence was visible to the eye. Before exhibiting visually discernable luminescence, the oxygen concentration had to be reduced to ~1% or less. Thereafter, the intensity visibly increased the lower the oxygen level was driven by the $N_2$ flush gas. This example demonstrates that the oxygen-sensitive indicator-polymer provides means to visually sense the oxygen content and changes in oxygen in the environment in which it is placed.

Additionally, the thin film indicator-polymer samples described were exposed in air to flowing streams of $N_2$ flush gas blown through a nozzle directed at the samples. It was visually distinguishable, under Blacklight illumination, that the luminescence engendered was most intense at the center of the nitrogen gas directed stream. The intensity diminished in an oxygen concentration dependent manner the further the distance radially from the center point. These examples thus further demonstrate that the indicator polymer provides means to identify the presence or locale of leaks in an environment in either of two manners: via oxygen's escape causing quenching in a low-oxygen environment; or via escape of non-quenching gas, such as $N_2$ or $CO_2$, into an oxygen rich environment thereby causing localized displacement of the oxygen quencher.

EXAMPLE 5

This example provides the results from testing multilayered film structures made as laminates containing a layer of indicator-polymer and an oxygen-barrier. The indicator-polymer used in this example was PtOEP-Dowlex 2245. It was in the form of a thin film, made as an extruded press plaque from PtOEP Masterbatch #1, as described in Example 2.

Figure 6:
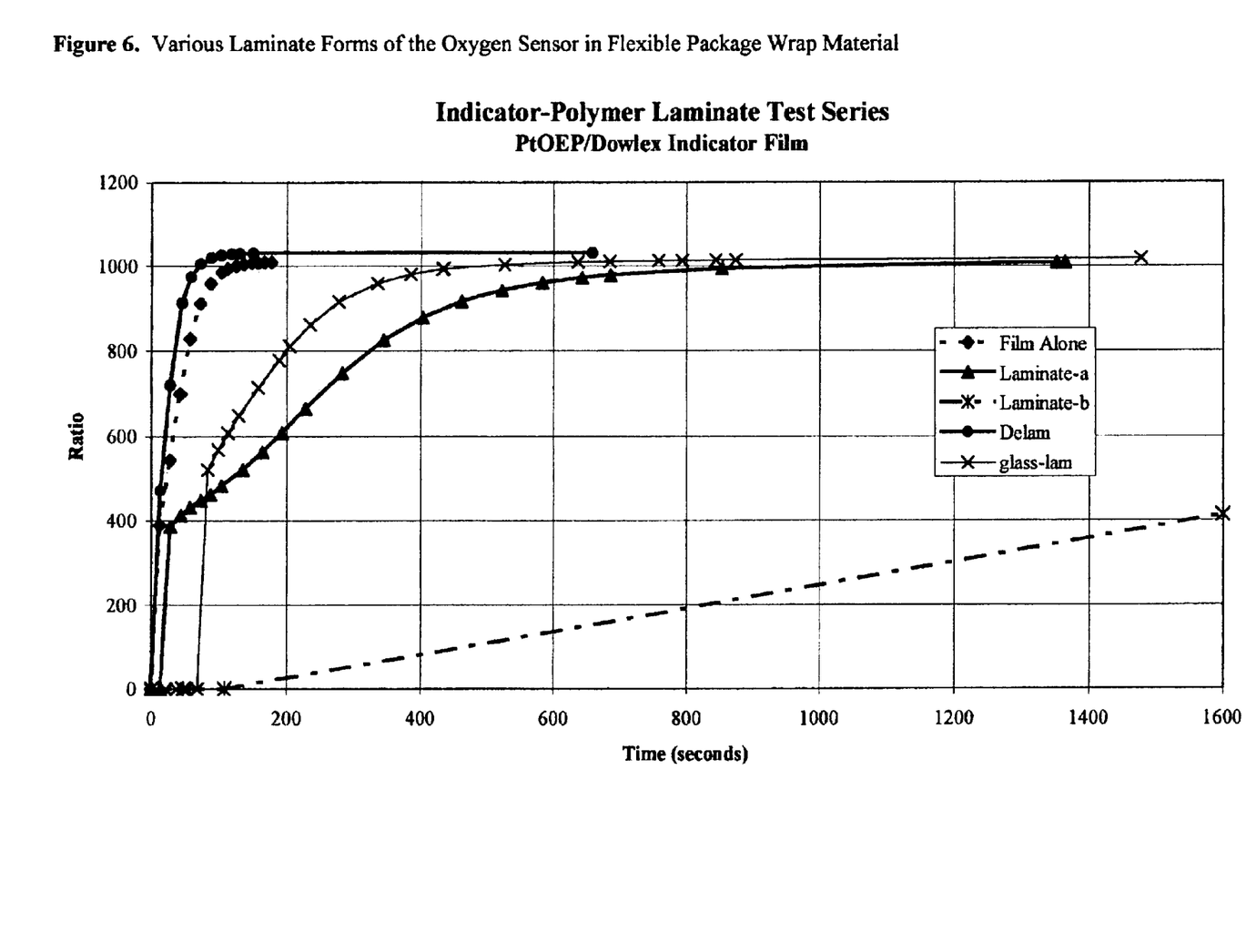
FIG. 6 shows that an indicator-polymer film in a multi-layer laminate configuration—(see Example 5). The film responds to changes in oxygen concentration and does so to essentially the same level (ratio) as the indicator-polymer film as a monolayer.

In a first test, the indicator-polymer film was loosely taped at its edges to the window of the gas-flush test chamber described herein (Instrumentation for Luminescent Lifetimes). Nitrogen was flushed into the gas-flush test chamber and the change in the signal ratio of the indicator-polymer film was measured as a function of time. The results are shown in FIG. 6 as "Film-Alone". The sensor responded quickly to a $N_2$ flush, reaching 95% of its final value within 60 seconds. This illustrates the capability of the indicator-polymer film when used by itself as a monolayer, to measure oxygen within the environment to which it is exposed.

Following this test, the indicator-polymer film was heat laminated to a multilayer oxygen-barrier flexible wrap film obtained from a commercially available modified-atmosphere food package ("Ready Crisp Bacon", SHK, Inc.). To laminate, the package oxygen-barrier film was placed on a hot-plate with its food-contact layer's surface facing up and the indicator-polymer film was placed on this surface. The two films were lightly pressed together and heat bonded to one another eliminating bubbles and wrinkles to form multilayer laminate-a. The laminate-a was tested using the gas-flush test chamber previously described, but in this case the chamber was modified by removing the glass window from the port used for optical interrogation of the sample within. Laminate-a was mounted in the open port of the modified gas-flush test chamber such that the indicator-polymer film was exposed internally to the gas contents inside the chamber. The opposing side of laminate-a, bearing the oxygen-barrier film, was externally exposed to ambient air. The gas-flush test chamber was purged with nitrogen flush gas.

The result shown in FIG. 6 demonstrates that the indicator-polymer film in the configuration of multilayer laminate-a still responded to changes in oxygen concentration and did so to essentially the same level (ratio) as the indicator-polymer film when by itself as a monolayer (the first test above). As expected, the response time characteristic of the indicator-polymer film in the laminate configuration was slower than by itself as a monolayer since the multilayer oxygen-barrier film impedes oxygen transfer via its bonded side. Nonetheless, the example shows that the indicator-polymer film in the laminate retains response characteristics similar to its monolayer form and would serve to measure the internal oxygen contents of a package or vessel.

Also shown in FIG. 6 as "Laminate-b" is the response of the indicator-polymer film in the laminated configuration last described above, but in this case the indicator-polymer film was further covered on its exposed surface with a layer of "Scotch-tape" adhered over it—a relatively gas impermeable barrier material. In this configuration, laminate-b, the indicator-polymer film layer was thereby "sandwiched" between the multilayer oxygen-barrier film and the tape that is obstructing its exposure to the environment to be sensed. The laminate-b sample was attached to the open port of the gas-flush test chamber in the same manner as the previous laminate test example and the chamber purged with nitrogen gas while monitoring the indicator-polymer film's signal response. The results indicate that the indicator-polymer film in laminate-b configuration registered a lower ratio, indicating a higher oxygen concentration within the indicator-polymer film layer, than observed on the previous films' tests at equivalent times throughout the test period (over 1600 seconds). This last example serves to illustrate that the indicator-polymer can be use for not only measuring the internal package oxygen contents, but also the kinetics of oxygen within film structures. Because the indicator can be placed in most, if not all the film's internal layers, this feature is exploitable to usefully measure the oxygen permeation rates through various film layers and different polymers. Furthermore, by continuous monitoring of change in oxygen within a structure, valuable insights regarding active processes occurring internally in the film (e.g. hydration, decomposition, oxygen scavenging) are gained.

EXAMPLE 6

The curve labeled "Delam" in FIG. 6 shows the result of peeling apart the film layers in the multilayer laminate-b, and retesting the indicator-polymer film by itself again loosely fixed to the glassed window of the gas-flush test chamber as was done in the first case of Example 5. As observed, the delaminated indicator-polymer film in the repeat test demonstrated essentially the same response characteristics as shown previously. This indicates that the indicator-polymer oxygen response characteristic remained consistent and that the results of the various test sample configurations were due to the nature of the various structures and not an intrinsic change in the indicator-polymer film.

EXAMPLE 7

The indicator-polymer film of Example 5 was heat laminated by itself directly onto the gas-flush test chamber's glass window that represents a highly efficient oxygen-barrier material that contains negligible oxygen. The chamber was purged with nitrogen gas and the change in the signal ratio of the indicator-polymer film measured as a function of time in the same manner performed in Examples 5 and 6. The results are presented as "glass-lam" in FIG. 6. As expected the indicator-polymer film in the glass-lam configuration was slower to respond to oxygen change in contrast to the indicator-polymer film by itself (see Example 6 "delam", and the "film alone" of Example 5, indicated in FIG. 6). The glass-lam results were similar to those shown for the Bacon package's oxygen-barrier film laminate with the indicator-polymer (laminate-b of Example 5); albeit perhaps the glass-lam's response to nitrogen flushing was slightly faster, perhaps since glass does not harbor entrapped oxygen that would slow the response. Comparison of the glass-lam, laminate-b and indicator-polymer "film alone" results suggest that an important factor in the response times of the films (although not their equilibrium responses) is the diffusion area, i.e. whether film is exposed on both sides or only one side to the gas environment. Further, though, these results show that the indicator-polymer film response is modulated by the oxygen content surrounding it.

EXAMPLE 8

This example describes how the process of melting an indicator into a polymer can serve to demonstrate that melting, or thermal bonding, such as in heat sealing operations, has occurred. PtTFPP indicator was dissolved into methanol at 50 ug/ml. Two press-plaque films of Dowlex 2245 were prepared, as described in Example 2, but without incorporating indicator into the polymer melt. The PtTFPP indicator solution was administered to the surface of one plaque and allowed to evaporate. Since the methanol did not dissolve the Dowlex polymer, the indicator was left deposited as a coating on the surface of the plaque at a concentration of approximately 4 ug/cm$^2$. The indicator coating in this state exhibited no visible luminescence when examined under a Blacklight (as described in Example 4) even when exposed to a N$_2$ gas flush.

The plaque surface with the indicator coating was overlaid with the other Dowlex press-plaque film also made without indicator, such that the coating was sandwiched between the two polymer film pieces. A portion of the two-plaque sandwich was exposed to localized heating to 230° C., sufficient to melt and bond the two plaques together at the region where the heat was applied. Visual examination of the melted region under the Blacklight revealed that indicator luminescence could be seen, but only in the bonded region of the press-plaques. Luminescence could not be distinguished where melting and bonding did not occur.

We claim:

1. A multi-layered food packaging film having an ability to detect oxygen presence within a packaging material, comprising an indicator polymer product film and a plurality of non-oxygen sensing polymer films bonded thereto, wherein the indicator polymer product film is made by a process comprising:

(a) adding an oxygen-sensitive indicator to a thermoplastic polymeric material heated to just above its melting temperature;

(b) mixing the oxygen-sensitive indicator thoroughly within the thermoplastic polymeric material while continuing the heating to maintain the thermoplastic polymeric material in a substantially liquid form; and (c) forming the mixture into an end product form of indicator-polymer product.

2. The multi-layered food packaging film of claim 1 wherein the forming step is accomplished by an extrusion process, a molding process or an injection molding process.

3. The multi-layered food packaging film of claim 1 wherein the oxygen-sensitive indicator is selected from the group consisting of polycyclic aromatic hydrocarbons, pyrene, fluoranthene, decacyclene, diphenylanthracene, benzo(g,h,i)perylene), porphyrins, platinum or palladium octaethylporphyrin, tetraphenylporphyrin, tetrabenzporphyrin, chlorins, bacteriochlorins, isobacteriochlorins, chlorophyll), and combinations thereof.

4. The multi-layered food packaging film of claim 1 wherein the polymeric material is selected from the group consisting of linear ethylene alpha olefin copolymers, ethyl vinyl acetate, LLDPE, VLDPE metallocene catalyzed polymers, and combinations thereof.

5. The multi-layered food packaging film of claim 1 wherein the melting temperature is from about 140° C. to about 240° C.

* * * * *